United States Patent [19]

Johnson et al.

[11] Patent Number: 4,754,654
[45] Date of Patent: Jul. 5, 1988

[54] SUBMERSIBLE SEAWATER PUMP SAMPLER

[75] Inventors: Bruce D. Johnson; Peter J. Wangersky, both of Halifax, Canada

[73] Assignee: Canadian Patents and Development Limited, Ottawa, Canada

[21] Appl. No.: 1,432

[22] Filed: Jan. 8, 1987

[30] Foreign Application Priority Data

Jan. 9, 1986 [CA] Canada ................................. 499276

[51] Int. Cl.[4] .............................................. G01N 1/14
[52] U.S. Cl. ................................ 73/864.34; 73/864.67
[58] Field of Search ............ 73/864.34, 864.35, 864.67

[56] References Cited

U.S. PATENT DOCUMENTS 4,606,233  8/1986  Burney .......................... 73/864.34 X Primary Examiner—Tom Noland
Attorney, Agent, or Firm—Wenderoth, Lind & Ponack

[57] ABSTRACT

There is described a submersible water sampler for use in the collection of samples for testing. Conventional in situ samplers have had the disadvantage that they have been bulky and difficult to handle. There is described an in situ water pump sampler which has a frame member attached to a hydrographic wire by a swivel. The sampler is self-contained and is mounted through a hub to a frame member to permit rotation of the sampler on the frame about an axis normal to the longitudinal axis of the hydrographic wire. A mechanism, operated by messengers dropped from the surface causes incremental rotation of the sampler member on its frame from an initial lowering position in which the pump sampler member extends in a generally up-and-down configuration to an intermediate sampling position in which the pump sampler extends generally at right angles to the axis of the hydrographic wire and then to a final retrieval position in which the pump sampler member extends in the generally up-and-down configuration on its frame.

15 Claims, 7 Drawing Sheets

SUBMERSIBLE SEAWATER PUMP SAMPLER

BACKGROUND OF THE INVENTION

The present invention relates to water samplers of the type known as in situ pump samplers. The invention particularly relates to in situ pump samplers for trace substances in lake water or seawater, with a particular application to seawater.

The use of in situ concentration for various trace substances in seawater offers clear advantages over conventional methods requiring bulk water sample collection and shipboard extraction. For some substances of oceanographic, geochemical, or toxicological interest the degree of concentration required to ensure reasonable accuracy and precision of analysis necessitates the handling of very large volumes of sample. In the past, samplers have been built which collected thousands of liters of seawater and required twelve or more hours of station time for sampling and processing, in order to collect enough of some rare component for reliable analysis. For other components, large samples were needed in order to overcome the problem of large and variable background or blank values.

Until fairly recently, conventional methods of collection and concentration seemed adequate for most trace substances, since the analytical limits of detection exceeded apparent levels of contamination. However, a review of the earlier work reveals that in many instances contamination actually acquired during collection and extraction comprised the major part of the reported concentrations. For an even greater number of substances, more recent methods of analysis provide sensitivities which far exceed the capability of the most careful water sampling regime to deliver contamination-free samples.

An examination of the possible sources of contamination has provided insights useful in devising a more effective sampling strategy. The sources of contamination include the hydrographic wire carrying the sampling container and the sampling container itself. The early samplers, the Knudsen and Nansen bottles, used metal alloy valves requiring heavy application of stopcock grease, and were thus unfit for either trace metal or trace organic analyses. More recent samplers often contain both trace metals and plasticizers in the plastic used in their construction. The research vessel on station is surrounded by an aura of waste products through which the sampler must pass. Once the sample has been collected and brought on board for extraction, the usual hazards of contamination common to any laboratory are present, augmented by those special contaminants resulting from shipboard operations.

The oceanographic literature provides evidence of the considerable effort expended in attempts to reduce contamination. Hydrographic wires encapsulated in polymers, or made of materials such as Kevlar (Trade Mark) have been described, as have samplers made of noncontaminating materials or employing a large volume/ internal surface ratio. Remote sampling buoys have been utilized, and clean rooms have been fitted to some research vessels. While all of these strategies for avoiding sample contamination have met with some success, they suffer from the limitations of inconvenience, high cost, lack of versatility, and the need for large vessels with special winches or adequate deck space. At a time when the availability and expense of big ship operation will inevitably force the oceanographic community, outside of the large government laboratories to do much of its sample collecting from ships of opportunity, these do not appear to be useful strategies for the university or the small government laboratory.

In situ pumping offers a means of concentrating various trace substances from seawater while diminishing much of the potential for contamination inherent in water sample collection and shipboard extraction. Furthermore, where large samples are desired, the volume sampled is limited only by the capacity of the power source and the efficiency and capacity of the method of concentration.

For many chemical entities, the concentrator of choice is some variety of adsorption column. In recent years the chemical literature has overflowed with reports of newer and better column packings, with capabilities for concentrating an ever-increasing list of trace substances.

Some studies in which in situ pumping has been used have been described in the oceanographic literature. While the great potential of the method is apparent from these publications, the pumping systems used are invariably large, heavy, and are powered either from the surface or by specially prepared lead-acid storage batteries.

A pumping system powered from the surface requires a winch carrying conductor cable and equipped with slip rings. Such winches are not common either on ships of opportunity or on the smaller oceanographic research vessels. If a reasonable amount of power is needed, the system must either be limited to shallower depths or it must transmit a very large voltage at the surface in order to overcome the power loss in transmission.

The lead-acid storage batteries typically used for in situ pumping have proven effective but both inconvenient and hazardous. These batteries require a means of pressure equilibration, and provision must be made for degassing and for insulation of their terminals.

To obtain the most out of in situ pumping versatility of the device must be considered. The pump sampler should be capable of pumping accurately whether large volume samples or small volume samples are involved. The system should be light and compact and should be of a nature such that more than one unit could be accommodated on a hydrographic wire in a single cast, so that depth profiles may be obtained, if desired, the system should be capable of activation and deactivation by a very simple contrivance and the device should be capable of alignment during operation to minimize the effects of sample contamination.

SUMMARY OF THE INVENTION

According to the present invention there is provided an in situ water pump sampler comprising a frame member; swivel attachment means for attaching the frame member to a hydrographic wire to permit 360° pivoting of the frame member about the longitudinal axis of the hydrographic wire; a self-contained pump sampler member; a hub-like means adapted to be mounted on the frame means to pivotally attach the pump sampler member to the frame means to permit rotation of the pump sampler member on the frame about a rotation axis normal to the longitudinal axis of the hydrographic wire; and means responsive to sequential command signals to permit incremental rotation of the pump sampler member on the frame member about the rotation axis from an initial lowering position, in which the pump sampler member extends in a generally up-and-down configuration, to an intermediate sampling position, in which the pump sampler member extends it generally at right angles to the longitudinal axis of the wire, to a final retrieval position in which the pump sampler member extends in a generally up-and-down configuration on the frame.

Preferably the pump sampler member is generally of tubular configuration, generally radiating, spoke-like from the hub-like means; and includes a water sample pump having a pump head on the distal end of the pump sampler member, which pump head is located above the hub-like means in the initial lowering position and below the hub-like means in the retrieval position.

According to a preferred embodiment the frame member is a rectangular plate-like member with the hub-like means being disposed substantially centrally of, and extending through, the plate-like member.

According to a feature of the invention directional vanes may be provided at one end of the tubular configuration pump sampler means, the vanes being responsive to the action of water currents, when the device is submersed and deployed in its intermediate sampling position, to orient the pump sampler relative to the longitudinal axis of the hydrographic wire on the swivel attachment means to pivot the pump head into the current, upstream of the wire.

In a preferred configuration the hub-like means includes bearing members for pivotally attaching the pump sampler member on the hub-like means; and a trigger operated indexing mechanism is provided for locking the pump sampler member in the hub-like means in each of the lowering, intermediate and retrieval positions.

According to a further preferred feature of the invention the pump sampler member is mounted in a rotationally out-of-balance manner on the hub-like means and a trigger actuating mechanism is mounted on the frame so as to operatively engage and actuate the indexing mechanism in response to sequential command signals generated by primary messengers dropped down the hydrographic wire.

According to still a further preferred feature of the invention the bearings include means to attach secondary messengers and to release them sequentially in response to the signals generated by the primary messengers whereby to drop the secondary messengers down the hydrographic wire to activate a secondary in situ pump sampler therebeneath on the wire.

In order to provide for greater flexibility of operation, the water sample pump is preferably provided with a plurality of interchangeable pump parts to vary its pumping capacity.

Additionally, the water sample pump head may be adapted to receive a sample concentrating column.

The water sample pump conveniently may be provided with inlet and outlet flow lines; a one way valve member in the inlet and in the outlet flow line and actuated on initiation of pumping action by the water sample pump to open and permit commencement of water sample taking, and, on termination of pumping action, to close and seal the lines.

Furthermore the pump sampler means may include a self-contained battery pack to operate the water sample pump and preferably is provided with a visual counter to display elapsed time of pumping.

In order to extend the operating time of the water sample pump, the invention also envisages the provision of an extended life battery pack attachable to the frame.

BRIEF DESCRIPTION OF THE DRAWINGS

The following is a description by way of example of certain embodiments of the present invention reference being had to the accompanying drawings in which:

FIG. 4a is a detail of part of apparatus shown in FIG. 4;

DESCRIPTION OF THE PREFERRED EMBODIMENT

Figure 1:
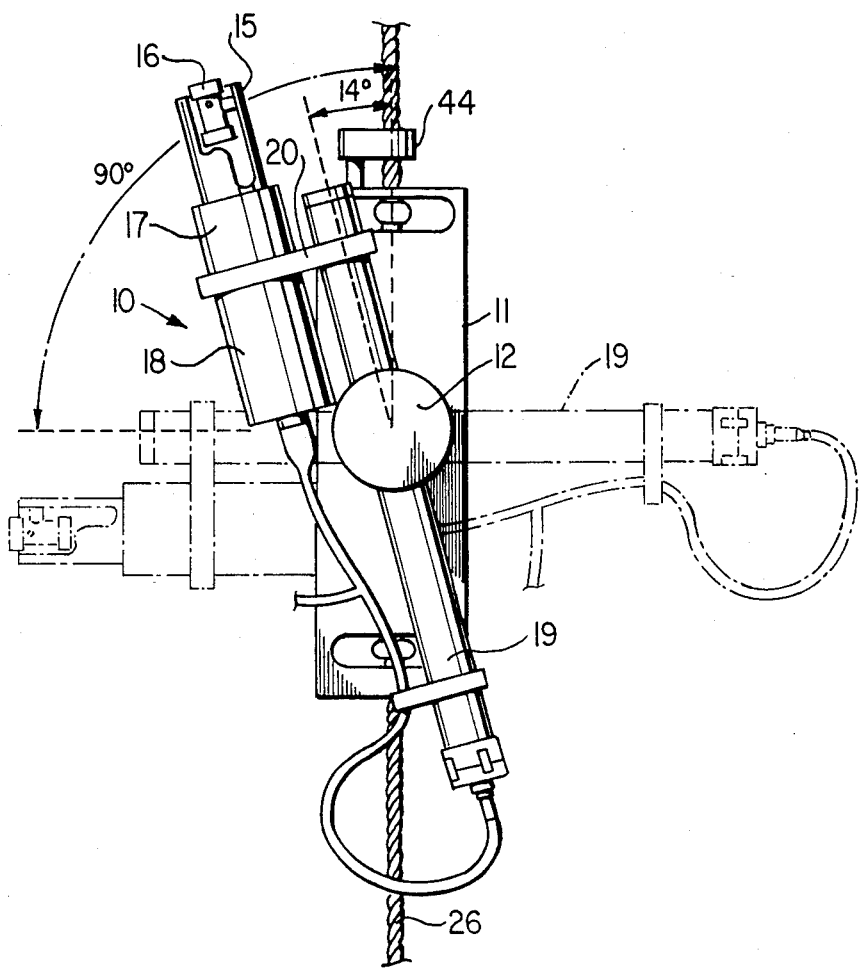
FIG. 1 is a schematic representation of the in situ pump sampler device in an initial lowering position, an intermediate, sampler, position being shown in chain dotted lines.

Turning now to the drawings.

An in situ pump sampler member 10, generally of tubular configuration, is mounted on a rectangular plate-like frame member 11 by means of a hub-like member 12. The pump sampler member 10 includes a water sample pump 15 provided with interchangeable heads 16 at the distal end of member 10, providing for a variety of pumping rates. The water pump 15 is driven by an electric motor 17 housed in the tubular continuation 18. The motor 17 is powered by batteries (preferably NiCad batteries) in a tubular electronics pack 19 also forming part of the pump sampler member 10 and braced thereto by brace member 20 to form a unitary body. The pump sampler member 10 radiates spoke-like from the hub-like member 12.

Figure 2:
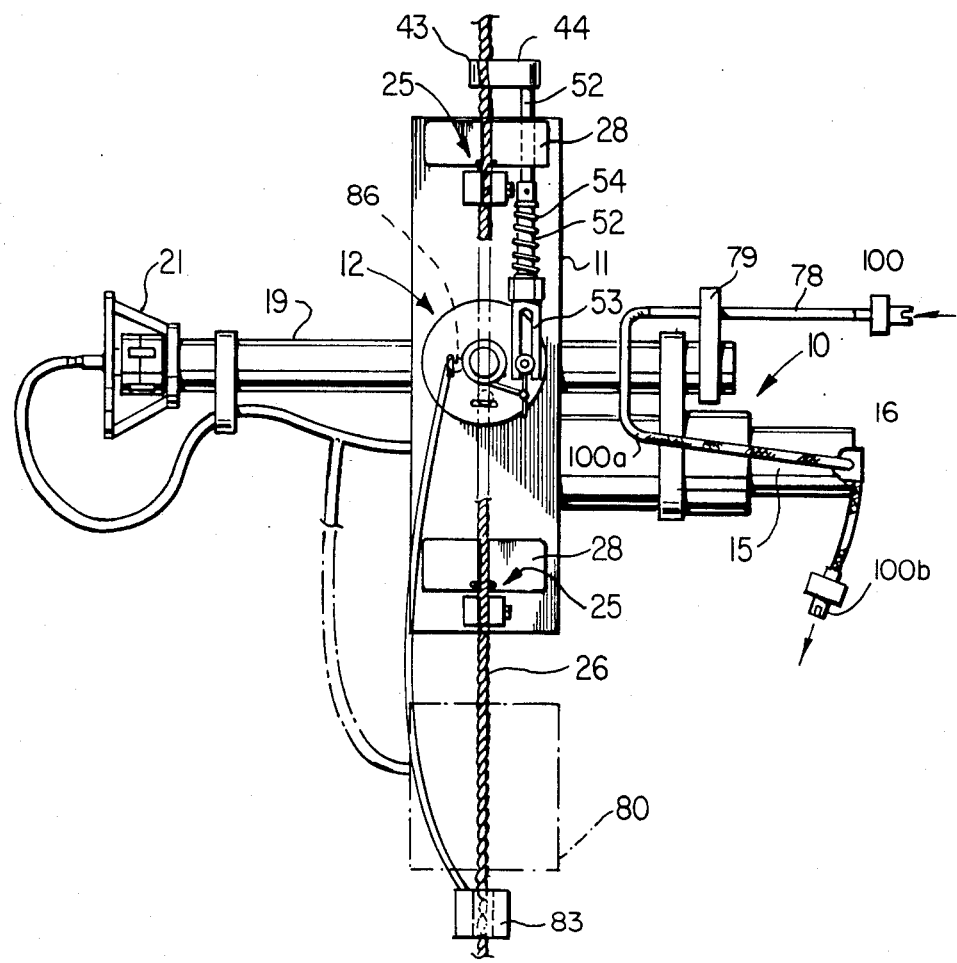
FIG. 2 is a view similar to FIG. 1 but taken from the other side of the device and showing the pump sampler deployed in its intermediate, or sampling, position.
Figure 5:
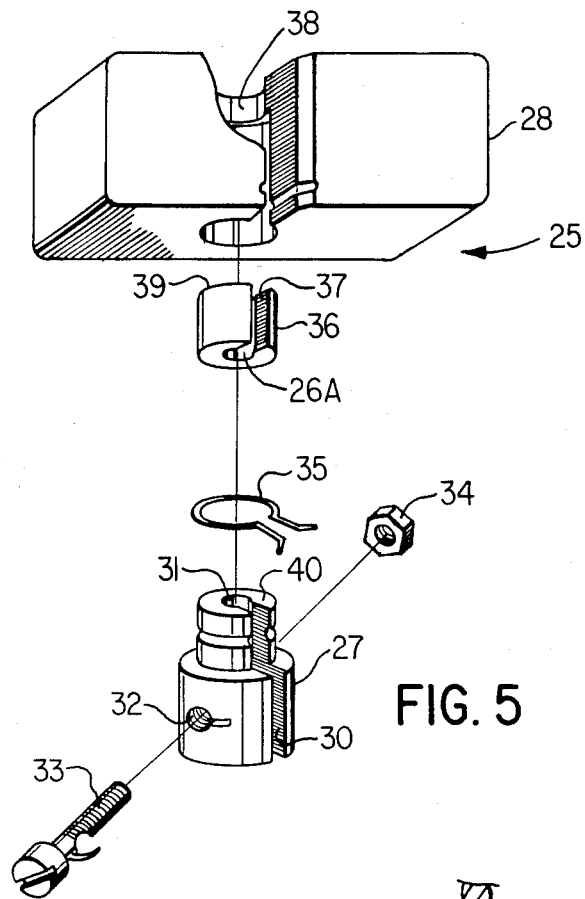
FIG. 5 is a detail, exploded, view of the swivel mounting for mounting the pump sampler on a hydrographic wire.
Figure 6:
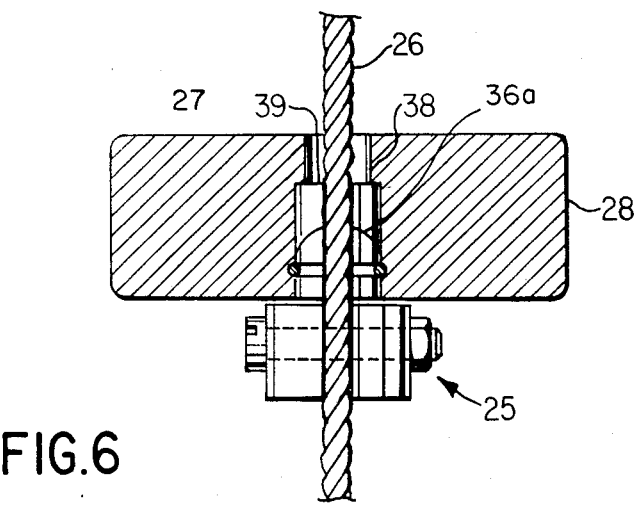
FIG. 6 is a detail of the parts shown in FIG. 5 assembled on the hydrographic wire.

Turning to FIGS. 2, 5 and 6, the frame member 11 is provided with two swivel mount members generally indicated at 25, for attachment of the pump sampler member 10 to a hydrographic wire 26 to permit a full 360° rotation of the frame 11 and its pump sampler member 10 about the longitudinal axis of the hydrographic wire 26. The swivel 25, and there are two of them, as seen in FIG. 2, comprises a wire clamp 27 located in the base of block 28. The wire clamp 27 is made of Delrin (Trade Mark) has a vertical slot 30 leading to a central axial bore 31 that accommodates the hydrographic wire 26. Normal to the hydrographic wire 26 in a slotted hole 32 is a holding bolt 33. Tightening the bolt 33, by its nut 34, secures the bolt 33 and by it, the clamp 27 to the wire 26 (see FIG. 6). The wire clamp 27 is clipped into position in block 28 with spring clip 35. Housed within the block 28 above the clamp 27 is a bearing block 36 made of Delrin. The clamp 27 has a conical nose 27a (see FIG. 6) which interfaces with a correspondingly conical shaped recess 36a in the underside of block 36 and provides an impetus for centering clamp 27 on block 36. The bearing block 36, like the clamp 27, has a central hydrographic wire passing bore 26A and communicating slot 37. The block 28 has an inwardly directed weight transmitting ledge 38 against which the upper face 39 of the bearing block 36, abuts. When the swivel 25 is clamped, by means of the bolt 33 to the hydrographic wire 26 and is attached by means of spring clip 35 to block 28 the weight of the pump sampler is transferred from block 28 to face 39 of bearing block 36 and from the underface of bearing block 36 to the upper face 40 of member 27. Thus the pump sampler 10 mounted on its frame 11 is clamped the hydrographic wire 26 by swivels 25 but because of the configuration of the swivel, the frame 11, with the pump sampler unit 10, is free to rotate a full 360° about the longitudinal axis of the hydrographic wire 26 on the relatively friction free Delrin faces. The pack 19 has orienting vanes or fins 21 (see FIGS. 2 and 3) which respond to the action of water currents and act to rotate the pump sampler 10 on its swivel about the wire 26 to point the pump head 16 into the current, upstream of wire 26.

Figure 3:
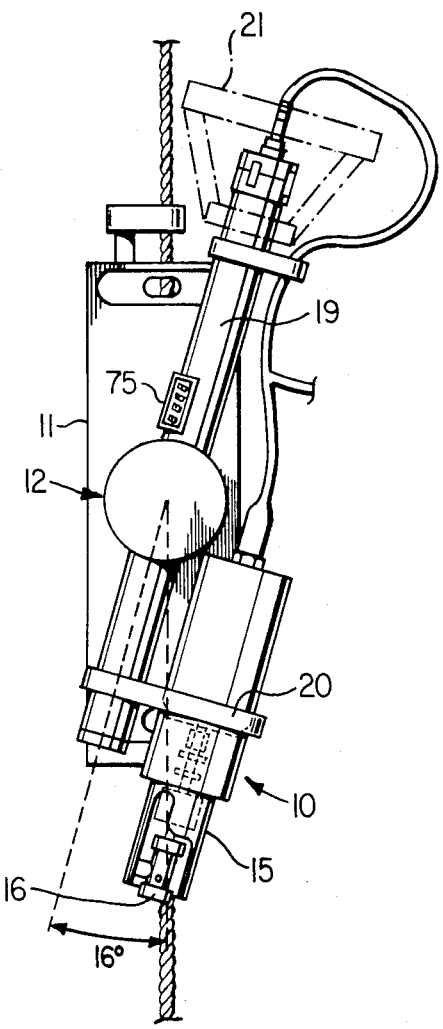
FIG. 3 is a view similar to FIG. 1 but with a pump sampler in a third, or retrieval position.
Figure 4:
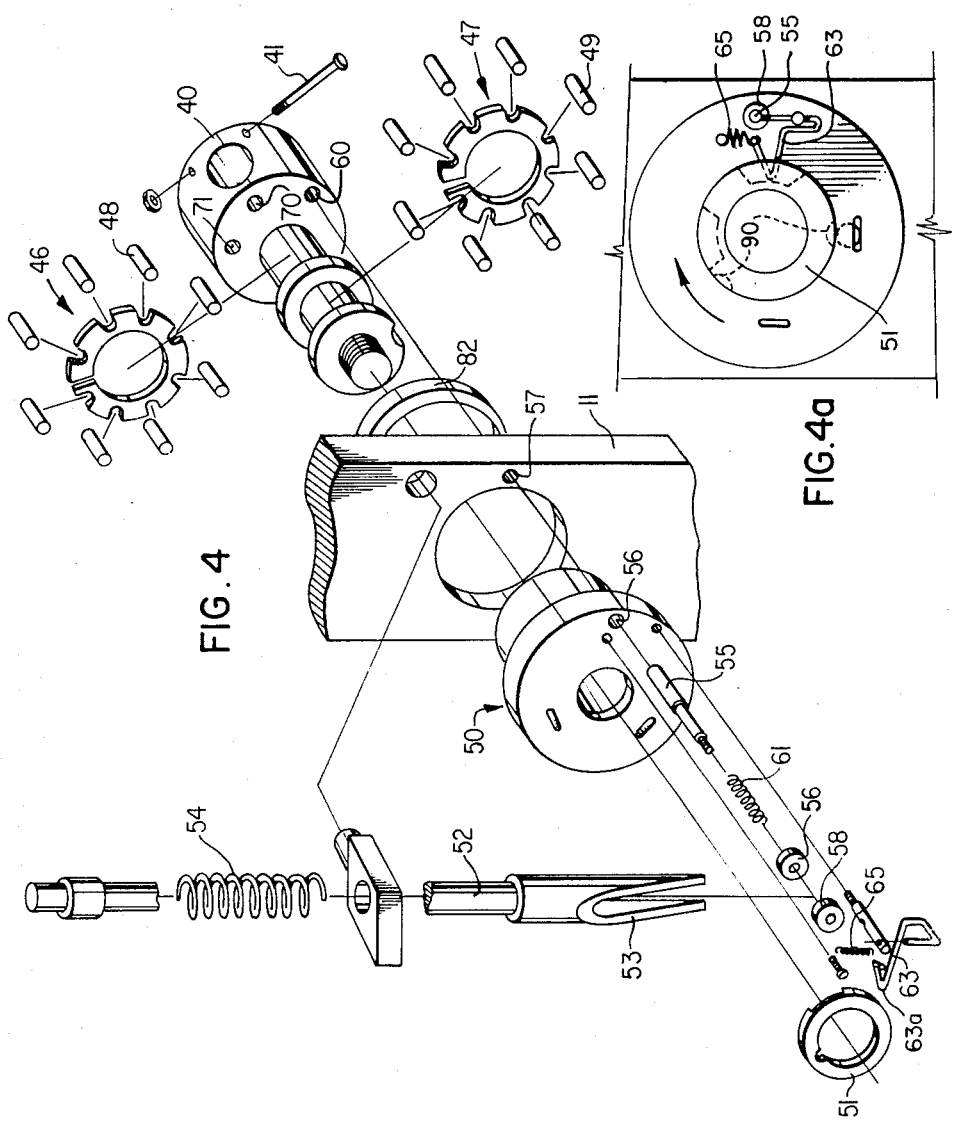
FIG. 4 is a detail, exploded, view of the means for mounting the pump sampler on its frame.

Referring now to FIGS. 1, 2, 3 and 4. The pump sampler unit 10, including its electronics pack 19 (which conveniently has a titanium housing), is mounted on hub-like member 12 so as to radiate spoke-like therefrom. As best seen in FIG. 4, tubular pack 19 passes through the bore in split collet 40 in hub-like member 12 and is locked therein by means of a nut and bolt clamping arrangement 41.

As is seen in FIGS. 1, 2 and 3 the pump sampler unit is mounted to occupy three indexed positions. The first position, as seen in FIG. 1, is the condition in which the pump sampler is lowered on the hydrographic wire to the desired sampling depth. Here the pump sampler unit 10 occupies a generally up-and-down position on frame 11. As seen in FIG. 1 the position of the pump sampler 10 is actually off-set, say, 14° to the vertical. When it is desired to start sampling the water, the pump sampler 10 is caused by means to be described hereinafter, to rotate, under its own weight (it being mounted in an out-of-balance condition) about a rotation axis of the hub normal to the longitudinal axis of the wire 26 to an intermediate, sampling, position in which the pump sampler member 10 extends generally at right angles to the longitudinal axis of the hydrographic wire 26 (see chain dotted line configuration in FIG. 1 and full line condition in FIG. 2). Here the pump sampler is locked in position until such time as it is decided to retrieve the pump sampler, at which time the indexing mechanism, to be described, is operated to permit the pump sampler unit 10 to occupy a third, retrieve position (see FIG. 3) in which the pump sampler is generally in an up-and-down condition, as shown in FIG. 3, at an angle of, say, 16° from the vertical.

Although it is to be understood that the pump sampler unit 10 could be mounted on the hub 12 so as to be rotatably driven by any suitable means, such as a stepping motor, in response to signals from the surface, it is preferred to effect the locating of the pump sampler 10 relative to its frame 11 by means of the inventive construction now to be described.

In FIG. 2 it will be noted that the hydrographic wire 26 passes through a canted slot 43 in an impact plate 44 and into a vertical hole in the plate 44. The canted slot 43 ensures that the vertical hydrographic wire 26 will not become disengaged from impact plate 44. This arrangement enables a messenger dropped down the hydrographic wire 26 from the surface, to hit the impact plate 44. (Messengers are devices well known and often used to activate instruments in oceanography. They are usually made of brass and clip onto, and can fall rapidly down a sampling wire, or the like.)

Figure 10:
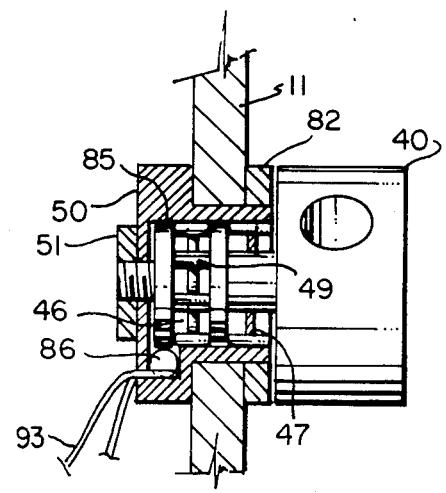
FIG. 10 is a cross-sectional view through an assembled structure of certain of the parts shown in FIG. 4.

Turning now more specifically to FIGS. 4 and 10. The hub-like member 12 includes bearings 46, 47 accommodating two sets of Delrin roller bearings 48, 49. These roller bearings 48, 49 have Teflon (trademark) keepers and facilitate rotation. The bearings are complete when the hub assembly passes into the receiver 50 thereof (with less than 0.005 centimeters clearance) and is secured by nut 51.

When a primary messenger is dropped from the surface down hydrographic wire 26 it contacts the impact plate 44 and transmits a command signal. Beneath the impact plate 44 and reciprocably mounted in the block of swivel 25 is a Delrin rod 52 carrying a slotted wedge 53 at its lower end. As will be clear from FIG. 4, the impact plate 44 with its rod 52 and slotted wedge 53 is maintained in a raised position by a compression trigger spring 54. In its normal position the slotted wedge 53 barely engages an indexing pin 55 straddling it between a washer 56 and threaded disc 58. However, when the messenger delivers a command signal to the impact plate 44 the rod 52 is driven downward by the impact of the messenger and the slotted wedge 53 forces the indexing pin 55 to slide in its hole 56 in the face of the fixed receiver member 50 and in its hole 57 in the plate-like frame 11 to which member 50 is anchored, and out of its indexing hole 60 in the rotating split-collet 40. The slotted wedge 53 in forcing the indexing pin 55 outwardly from hole 60, compresses return spring 61 and now that the indexing pin 55 is clear of the split-collet 40, the pump sampler 10, by its own weight, rotates in a clockwise fashion (as seen in FIGS. 2 and 4). The tip of a retaining spring 63 is forced by tension spring 65 to ride the surface of the threaded disc 58 and slips under the threaded disc 58 and thereby holds the indexing pin 55 out. This procedure ensures that the indexing pin 55 does not return to the hole 60 which it occupied before the messenger was dropped. Nut 51, which turns with collet 40 of the hub-like member 12, has slots in its edge which accommodate an elbow 63e on the retaining pin 63 (see FIG. 4a). When the pump sampler 10 has pivoted through all but a few degrees of its rotation prior to reaching its intermediate position, the slot in the nut 51 (see FIG. 4a) ends and the elbow of the retaining pin 63 is forced backwards pulling the tip of spring 63 from under disc 58 thus releasing the indexing pin 55. The indexing pin 55 is forced by its return spring 61 to ride the surface of the collet 40 between holes 60 and 70 until the next locking hole 70 is encountered. The pin 55 then slips into hole 70 and rotation is stopped and the pump sampler indexed in its intermediate, sampling, position. When the next sequential command signal is required, at the end of pumping and prior to retrieval, a second messenger is dropped down the hydrographic wire 26 again hits the impact plate 44 and the indexing operation is repeated, with the pump sampler rotating to the position seen in FIG. 3 for retrieval, at which point the indexing pin 55 will contact retaining hole 71.

The strength of the spring 54 is selected so that it compresses sufficiently upon impact of the first messenger to allow the indexing mechanism to disengage and operate but at the same time to be able to rebound, with the weight of the first messenger to allow the indexing mechanism to re-engage and lock the pump sampler 10. Further, after the second messenger makes contact with the impact plate 44, and the pump sampler has pivoted a second time, the spring 54 must be able to rebound carrying the weight of two messengers to allow the mechanism to index and lock in the third position.

Because of the high stress encountered in stopping the orientating rotation of the pump sampler 10 it is desirable that the indexing pin 55 be strong. A suitable material has been found to be in ultra high molecular weight polyethylene, a material with a very high Izod impact strength and yet with sufficient yield to absorb the impact.

The water pumping operation of the pump sampler 10 is controlled electronically by circuit components housed within pack 19. The control is based upon a clock module with a LCD display 75 (See FIG. 3). The electronic control circuit which is standard in design, preferably features a voltage reference and comparator for detecting low battery voltage, and an alarm detector circuit. A signal from either of these functions becomes latched, and by controlling a transistor which actuates a relay coil, disables the sampler until the system is recovered and reset. A magnetic switch (not shown) which turns the sampler pump 15 on, and which is triggered in conventional fashion by the rotation of the pump sampler 10 on its hub from the initial lowering position (FIG. 1) to the intermediate sampling position (FIG. 2), is located in series with a relay driver transistor; thus any of three functions, detection of low battery voltage, expiration of preset time interval, our arrival of the second messenger, terminates the pumping action.

The remainder of the electronic circuit provides control of the clock module. Starting the pump 15 enables the clock, and any of the aforementioned modes of pump termination stops the clock. Thus even if the pump stops before the preset time interval expires, the period in which the pump was active is recorded on LCD display 75.

The sample pump 15 conveniently may be an oil filled impeller pump operating on a 12 volt DC battery. In order to provide for the versatility required for sampling, a variety of pumpheads 16 have to be provided. Preferably the pump unit 15 should be capable of pumping a few hundred milliliters through a concentration column 78 (see FIG. 2) of reverse phase packing. Conveniently the concentration column 78 may be clamped to the electronics pack 19 with a holder 79. A water intake valve 100 (see also FIGS. 7, 7a and 8) is attached upstream of the column 78 which column, in turn, is connected to the head 16 by line 100a. Water outflow from the head 16 is through a line 100b and through water outlet valve 101 (see also FIGS. 7, 7a and 8). It will of course be understood that in conditions where a large column or filter is necessary it may be required to mount it on the frame 11 or wire 26. Since the pump 15 should also be capable of pumping hundreds of liters through a low pressure drop collector, such as the large filter, three interchangeable pumpheads 16 may be provided, the heads 16 having widely differing capabilities and being mounted so as to somewhat vary, at will, the performance of an individual head. Similarly a plurality of flow meters (not shown) need to be provided. Because of the difficulty of adapting flow meters to high hydrostatic pressures and also because of the complexity and expense of matching various meters to appropriate ranges of flow, two of the three pump heads 16 are preferably positive displacement, or metering, pumps. For such pump heads, and for flows not exceeding the pressure rating of the heads, the volume of seawater pumped is directly related to the period of pumping. The head that is not positive displacement should be used with a flow-meter.

In general, the materials of construction of the pump heads are not of great concern from the standpoint of sample contamination since the columns 78 and filters on which concentration is effected can be located upstream from the pump head as indicated in FIG. 2. Seawater contacts the pump 15 only after the substance of interest have been removed. In this mode of operation concern over materials of construction is limited to corrosion resistance. However, in rare instances where the pressure drop through the column 78 exceeds the hydrostatic pressure at the depth of sampling, cavitation can occur, and the column 78 would have to be located downstream of the pump (not shown). This situation can nearly always be avoided through careful choice of column and packing dimensions as well as flow conditions to produce pressure drops in the flow path of less than the ambient pressure. Where this problem cannot be avoided, as in near-surface pumping for trace organics enrichment on reverse phase sorbents, the column should be located downstream from the pump and the choice of material for pump head pump and piston is ceramic.

Figures 7, 7A, 8:
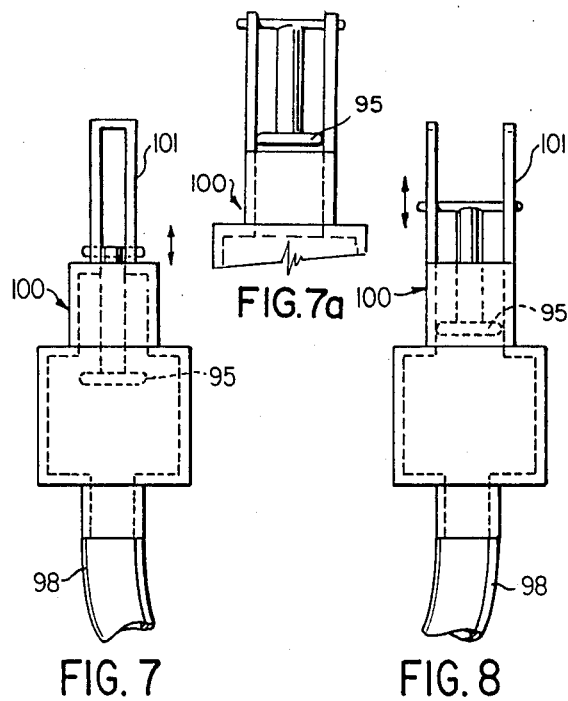
FIGS. 7 and 8 are details of one-way valve units provided in inlet and outlet water lines to the pump sampler.

Turning to FIGS. 7, 7a and 8 which show one suitable form of one-way valve 100 such as is mounted upstream of the column 78 and at the end of outflow tubing 100b (see FIG. 2). FIG. 7 shows the valve piston 95 open with the waterflow downward as seen in FIG. 7 by the directional arrow. FIG. 7a shows the position of the piston 95 when the water flow is reversed as shown by the directional arrow, and FIG. 8 shows the piston 95 in the "no flow" configuration. Thus when the device is placed on either inlet or outlet, the piston 95 is forced out of the narrow region of its cylinder by activation of the pump. Sea or lake water is then allowed to flow freely in the appropriate direction. Conveniently, the materials of construction are largely Teflon (trade mark) to avoid contamination.

An auxiliary battery pack, diagramatically shown at 80 (see FIG. 2), is clipped to the hydrographic wire 26 beneath the sampler frame 11. The purpose of the battery pack 80 is to extend the pumping life of the sampler.

Figure 9:
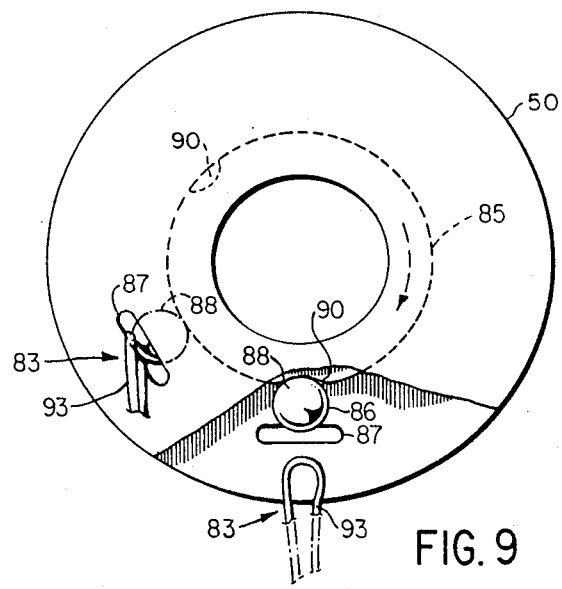
FIG. 9 is a detail of a mechanism for releasing secondary messengers from the pump sampler, down the hydrographic wire to a second in situ pump sampler positioned on the wire beneath it.

Referring now to FIGS. 2, 4, 9 and FIG. 10. In order to trigger a second pump sampler located on the hydrographic wire 26 beneath the first pump sampler (to permit sampling at different depths) the first pump sampler is provided with means, in the form of secondary messengers 83, releasable from the sampler 10 and permitting triggering of the sampler below. Ring 85 (see FIGS. 4 and 10) rotates with collet 40. In FIG. 9 it is shown how ring 85 can be modified to release the two secondary messengers 83 (only one of which is shown in FIG. 2) at the appropriate times. Slots 87 are cut into the face of receiver 50 (FIG. 4) to accept monofilament lines 93 which engage Delrin balls 88. Ring 85 normally holds the Delrin balls 88 against an internal flange in receiver 50 and stops the monofilament lines 93 that are attached to the secondary messengers 83 from escaping.

Dimples 90 are arranged on edge of ring 85. When the system is activated by the dropping of the primary messengers from the surface, rotation of the pump sampler from its initial position to its intermediate position causes ring 85 to rotate and when a dimple 90 aligns with a ball 88, the monofilament lines 93 thereof are permitted to escape, and the messenger 83 is dropped to a second pump sampler below. Slots 87 and dimples 90 are positioned so that one secondary messenger can be released when the sampler 10 is rotated from initial to intermediate position, and another secondary messenger can be released during rotation of the sampler 10 from intermediate to recovery position.

In operation the pump sampler 10 is lowered on its frame 11, clamped to the hydrographic wire 26, and the sampling column 78 is locked over the pumphead 16 in a position 14° from the vertical with the distal end of the sampler 10 pointing upwards (FIG. 1). When the sampling depth has been reached, a first primary messenger is dropped down the hydrographic wire 26 and contacts the impact plate 44. The command signal impulse from the messenger releases the locking mechanism and allows the pump sampler 10 to pivot about its hub 11. Under the eccentric weight of the pump 15, the sampler 10 in its collet 40 rotates in bearings 46, 47 into a horizontal position and the indexing mechanism acts to lock the pump inplace in the intermediate position (see FIG. 2). In this horizontal attitude the sampling inlet port for the column 78 is at the maximum distance from the hydrographic wire (the primary source of contamination from trace metals). When the pump sampler 10 with the pack 19 is locked in the horizontal position, the timing circuit and the pump are activated by the closing of a magnetic switch. Before deployment, the column filter and flow lines may be filled with pure water to avoid filling the column with contaminated surface waters while the system is lowered to depth and both the inlet and the outlet sealed (say by the non-return valves 100). With the starting of the pump the non-return valves 100 open and the sampling commences. Alternatively, in place of valves 100 tear away patches could seal inlet and outlet and be physically torn away by sampler rotation. When the sampling is completed, a second messenger is dropped down the hydrographic wire 26 and as the pump sampler starts to move from its horizontal position to its retrieval position, the magnetic switch is operated and the pumping is terminated. There is no need to close the inlet and outlet for recovery. The column 78 and pumphead 16 provide sufficient impedence to water flow. As a safety feature, the control could be arranged such that pumping is also stopped when the battery voltage falls below a predetermined level. However regardless of the motive termination of pumping, the elapsed time appears on the LCD display 75. With the pump sampler 10 rotated to its 16° position away from the vertical (See FIG. 3) the device is now ready for retrieval. As has been mentioned, if desired, a second, or a third, or more, pump samplers can be arranged on the hydrographic wire at appropriate depths to permit sampling at different levels.

What we claim as our invention is:

1. An in situ water pump sampler comprising a frame member; swivel attachment means for attaching said frame member to a hydrographic wire to permit 360° pivoting of said frame member about a longitudinal axis of said hydrographic wire; a self contained pump sampler member; a hub-like means adapted to be mounted in said frame means to pivotally attach said pump sampler member to said frame means to permit rotation of said pump sampler member on said frame about a rotation axis normal to the said longitudinal axis of said wire; and means responsive to sequential command signals to permit incremental rotation of said pump sampler member on said frame member about said rotation axis from an initial lowering position, in which said pump sampler member extends in a generally up-and-down configuration to an intermediate sampling position in which said pump sampler member extends generally at right angles to the longitudinal axis of said wire, to a final retrieval position in which said pump sampler member extends in a generally up-and-down configuration on said frame.

2. A device as claimed in claim 1 in which the pump sampler member is generally of tubular configuration, generally radiating, spoke-like, from said hub-like means; and includes a water sampler pump having a pump head on the distal end of said pump sampler member, which pump head is located above the hub-like means in the initial lowering position and below said hub-like means in said final retrieval position.

3. Apparatus as claimed in claim 2 in which directional vanes are provided at one end of said tubular configuration pump sampler means and responsive to the action of water currents when the device is in operation in its intermediate sampling position, to orient said pump sampler relative to the longitudinal axis of said hydrographic wire on said swivel attachment means to point said pump head into said current, upstream of said wire.

4. Apparatus as claimed in claim 2 in which said water sample pump is provided with a plurality of interchangeable pump parts to vary its pumping capacity.

5. Apparatus as claimed in claim 2 in which said water sampler pump head is adapted to receive a sample concentrating column.

6. Apparatus as claimed in claim 5 in which said concentrating column has inlet and outlet lines, and sealing means is provided to close said lines in said initial position and to open said lines when said pump sample member assumes said intermediate sampling position.

7. Apparatus as claimed in claim 2, in which said pump sampler means includes its own battery pack to operate said water sample pump.

8. Apparatus as claimed in claim 7 further including an extended life battery pack attachable to said frame for extending the operating time of said water sample pump.

9. Apparatus claimed in claim 7 in which said pump sampler means includes a visual counter to display elapsed time of pumping.

10. Apparatus as claimed in claim 2 in which said frame member is a rectangular plate-like member with said hub-like means being disposed substantially centrally of, and extending through, said plate-like member.

11. Apparatus as claimed in claim 1 in which said frame member is a rectangular plate-like member with said hub-like means being disposed substantially centrally of, and extending through, said plate-like member.

12. Apparatus as claimed in claim 1 in which said hub-like means includes bearing members for pivotally attaching said pump sampler member on said hub-like means; and a trigger operated indexing mechanism for locking said pump sampler member in said bearings in each of said lowering, intermediate and retrieval positions.

13. Apparatus as claimed in claim 12 in which said pump sampler member is mounted in a rotationally out-of-balance manner on said hub-like means and a trigger actuating mechanism is mounted on said frame so as to operatively engage and actuate said indexing mechanism in response to sequential command signals generated by primary messengers dropped down said hydrographic wire.

14. Apparatus as claimed in claim 13 in which said hub-like means include means to attach secondary messengers and to release them sequentially in response to said signals generated by said primary messengers whereby to drop said secondary messengers down said hydrographic wire to activate a secondary in situ pump sampler on the said wire therebeneath.

15. Apparatus as claimed in claim 1 in which said water sampler pump is provided with inlet and outlet flow lines; a one way valve member in said inlet and in said outlet flow lines and actuated, on initiation of pumping action by said water sampler pump, to open and permit commencement of water sample taking, and, on termination of pumping action, to close and seal said lines.

* * * * *